US00PP18851P2

(12) United States Plant Patent
Guillen

(10) Patent No.: US PP18,851 P2
(45) Date of Patent: May 27, 2008

(54) ***IMPATIENS* PLANT NAMED 'BALFAFORCH'**

(50) Latin Name: ***Impatiens flaccida*×*Impatiens hawkeri***
Varietal Denomination: Balfaforch

(75) Inventor: Mario Guillen, Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 67 days.

(21) Appl. No.: 11/602,762

(22) Filed: Nov. 21, 2006

(51) Int. Cl.
*A01H 5/00* (2006.01)

(52) U.S. Cl. ..... Plt./317

(58) Field of Classification Search ..... Plt./317
See application file for complete search history.

*Primary Examiner*—Annette H. Para
(74) *Attorney, Agent, or Firm*—Audrey Charles

(57) ABSTRACT

A new and distinct cultivar of *Impatiens* plant named 'Balfaforch', characterized by its lavender-colored flowers, medium green-colored foliage, and vigorous, trailing growth habit.

1 Drawing Sheet

Latin name of genus and species of plant claimed: *Impatiens flaccida*×*Impatiens hawkeri*.
Variety denomination: 'Balfaforch'.

BACKGROUND OF THE INVENTION

The present invention relates to a new and distinct cultivar of *Impatiens* plant botanically known as *Impatiens flaccida*× *Impatiens hawkeri* and hereinafter referred to by the cultivar name 'Balfaforch'.

The new cultivar originated in a controlled breeding program in Cartago, Costa Rica during December 2000. The objective of the breeding program was the development of *Impatiens* cultivars with numerous flowers, excellent basal branching, and a vigorous, mounded-trailing growth habit.

The new *Impatiens* cultivar is the result of cross-pollination. The female (seed) parent of the new cultivar is the proprietary *Impatiens flaccida* breeding selection designated NG5, not patented, characterized by its medium lilac-colored flowers, medium green-colored foliage, and trialing growth habit. The male (pollen) parent of the new cultivar is the *Impatiens hawkeri* Divine $F_1$ Series Lavender, not patented, characterized by its medium lavender-colored flowers, dark green-colored foliage, and mounded growth habit. The new cultivar was discovered and selected as a single flowering plant within the progeny of the above stated cross-pollination during July 2002 in a controlled environment at Cartago, Costa Rica.

Asexual reproduction of the new cultivar by terminal stem cuttings since July 2002 at Cartago, Costa Rica, Arroyo Grande, Calif, and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balfaforch' as a new and distinct cultivar of *Impatiens* plant:

1. Lavender-colored flowers;
2. Medium green-colored foliage; and
3. Vigorous, trailing growth habit.

Plants of the new cultivar differ from plants of the female parent primarily in flower color and from plants of the male parent primarily in flower color, foliage color, and growth habit.

Of the many commercially available *Impatiens* cultivars known to the inventor, the most similar in comparison to the new cultivar is Fanfare® Fuchsia Improved 'Balfafusimp', U.S. Plant Pat. No. 17,715. However, in side by side comparisons, plants of the new cultivar differ from plants of 'Balfafusimp' in the following characteristics:

1. Plants of the new cultivar are taller than plants of 'Balfafusimp';
2. Plants of the new cultivar are wider than plants of 'Balfafusimp'; and
3. Plants of the new cultivar have a flower color different from plants of 'Balfafumsimp'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfaforch'. The plants were grown in 4.5 inch pots for 17 weeks in a greenhouse at West Chicago, Ill.

DETAILED BOTANICAL DESCRIPTION

Figure 1:
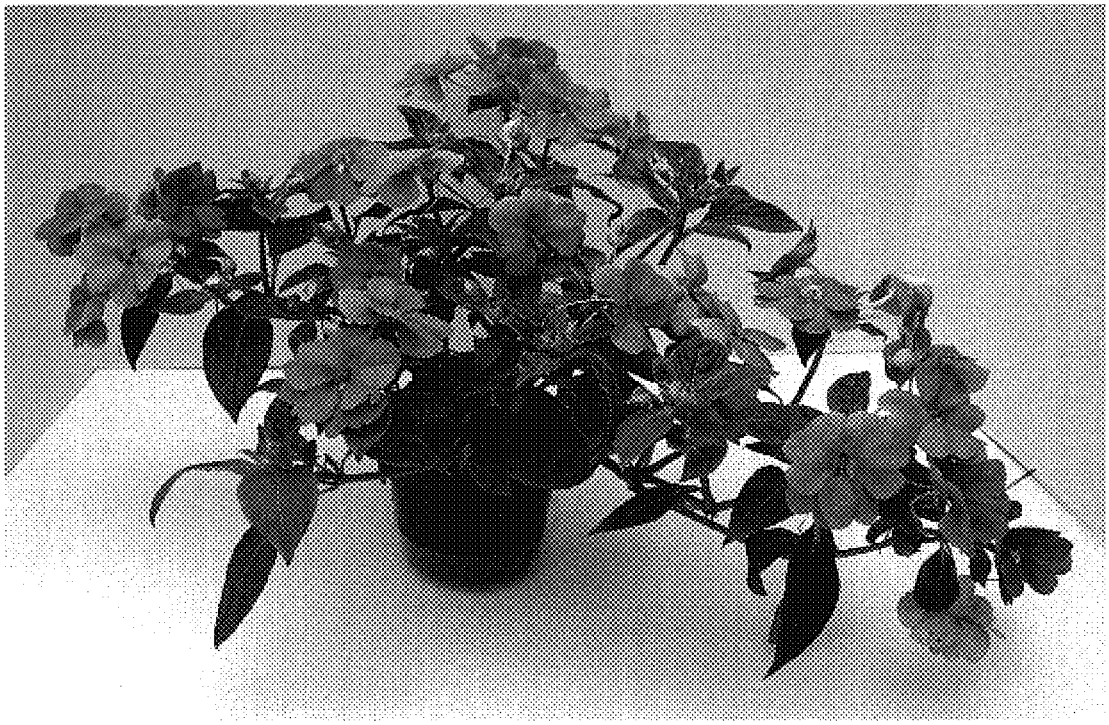
FIG. 1 illustrates a side view of the overall growth and flowering habit of 'Balfaforch'.
Figure 2:
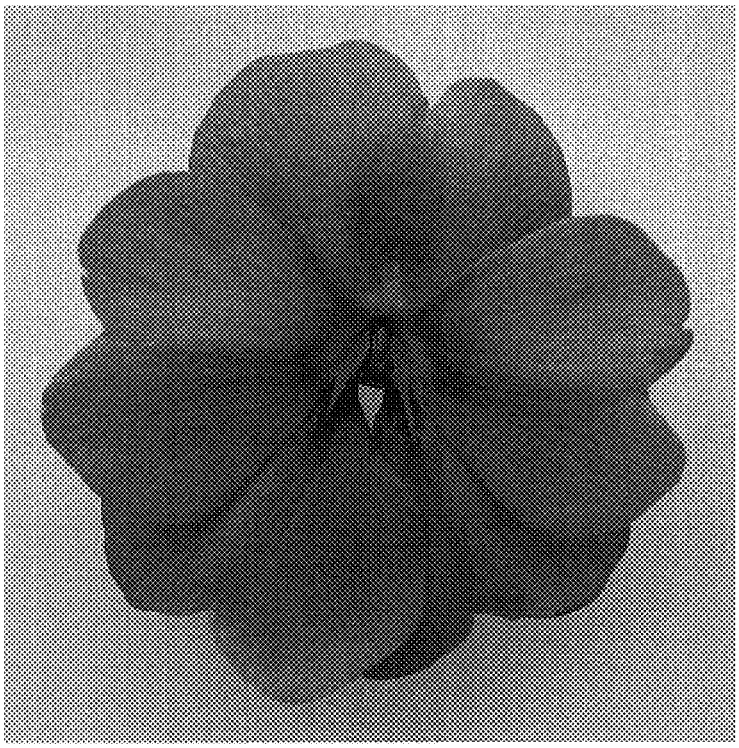
FIG. 2 illustrates a close-up view of an individual flower of 'Balfaforch'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Mar. 29, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 17 weeks utilizing a soilless grown medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens flaccida*×*Impatiens hawkeri* cultivar Balfaforch.

Parentage:

*Female parent.*—Proprietary *Impatiens flaccida* breeding selection designated NG5, not patented.

*Male parent.*—*Impatiens hawkeri* Divine $F_1$ Series Lavender, not patented.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 6 to 8 weeks from a rooted cutting.

*Growth habit and general appearance.*—Vigorous, trailing.

*Size.*—Height from soil level to top of plant plane: Approximately 18.1 cm. Width: Approximately 44.0 cm.

*Branching habit.*—Freely basal branching. Quantity of main branches per plant: Approximately 5.

*Branch.*—Strength: Strong. Length: Approximately 21.5 cm. Diameter: Approximately 4.6 mm. Length of central internode: Approximately 5.2 cm. Texture: Sparsely pubescent. Color of young and mature stems: 145A with overlay of 187B.

Foliage description:

*General description.*—Quantity of leaves per main branch: Approximately 9. Fragrance: None. Form: Simple. Arrangement: Opposite or in whorls of 3 to 5.

*Leaves.*—Aspect: Perpendicular to stem. Shape: Elliptic. Margin: Serrate, ciliate. Apex: Acuminate. Base: Attenuate. Venation pattern: Pinnate. Length of mature leaf at center of stem: Approximately 8.7 cm. Width of mature leaf at center of stem: Approximately 4.0 cm. Textures of upper and lower surfaces: Glabrous. Color of upper surface of young foliage: Closest to 139A at center transitioning to 138A at margins with venation of 144C. Color of lower surface of young foliage: Greener than 191B with venation of 144D. Color of upper surface of mature foliage: Closest to 139A with venation of 144B. Color of lower surface of mature foliage; 191B with venation of 144D.

*Petiole.*—Length: Approximately 1.5 cm. Diameter: Approximately 2.0 mm. Texture: Glabrous. Color: 144D with an overlay of 187B.

Flowering description:

*Flowering habit.*—'Balfaforch' is freely flowering under outdoor growing conditions with substantially continuous blooming from spring through autumn and year-round in greenhouse environment.

*Lastingness of individual flower on the plant.*—Approximately 10 to 12 days.

Flower description:

*General description.*—Type: Single. Quantity per plant: Approximately 27. Fragrance: None.

*Bud.*—Rate of opening: Generally takes 1 to 2 days for bud to progress from first color to fully open flower. Quantity showing color per plant: Approximately 4.

*Bud just before opening.*—Shape: Ovoid. Length: Approximately 1.9 cm. Diameter: Approximately 1.4 cm. Color: Lighter than N78D.

*Corolla.*—Shape: Round, slightly cupped when first open with petals turning downward with age. Width: Approximately 5.9 cm. Depth: Approximately 1.5 cm. Borne: Above foliage.

*Petals.*—Quantity: 5. Shape: Obovate. Aspect: Flat. Appearance: Iridescent. Margin: Entire. Apex: Emarginate with an acuminate tip in the center. Base of upper petal: Truncate. Base of lateral and lower petals: Attenuate with each lateral petal fused to a lower petal at base. Length of upper petal: Approximately 2.5 cm. Width of upper petal: Approximately 4.0 cm. Length of lateral petals: Approximately 2.7 cm. Width of lateral petals: Approximately 3.1 cm. Length of lower petals: Approximately 3.0 cm. Width of lower petals: Approximately 3.5 cm. Texture of upper and lower surfaces: Glabrous. Color of upper surface when first open and fully open: N78B with a small area of N79C at the base of the two lower petals. Color of lower surface when first open and fully open: N78D.

*Spur.*—Quantity: 1 per flower. Length: Approximately 4.8 cm. Diameter at tip: Approximately 1.0 mm. Diameter at base: Approximately 2.0 mm. Texture: Glabrous. Color: 186C with tip of 144D.

*Peduncle.*—Strength: Strong. Aspect: Acute angle to stem. Length: Approximately 4.3 cm. Diameter: Approximately 2.0 mm. Texture: Sparsely pubescent. Color: 144D.

*Sepals.*—Quantity per flower: 4, with one fused to base of upper petal. Shape of lateral and lower sepals: Ovate. Apex of all sepals: Acuminate. Length of lateral sepals: Approximately 1.2 cm. Width of lateral sepals: Approximately 5.2 mm. Length of lower sepal: Approximately 1.8 cm. Width of lower sepal: Approximately 1.0 cm. Texture of upper and lower surfaces of all sepals: Glabrous. Color of lateral sepals: 144C at apex transitioning to 155C at base. Color of lower sepal: N155B with 144D at tip of apex.

*Reproductive organs.*—Androecium: Stamen quantity: 5 per flower, fused around pistil at apex. Anther shape: Hooded. Anther length: Approximately 1.0 mm. Anther color: N78B. Pollen amount: None observed. Gynoecium: Pistil quantity: 1 per flower. Pistil length: Approximately 5.2 mm. Stigma shape: 5-pointed star. Stigma color: Colorless, translucent. Style color: 144D. Ovary texture: Glabrous. Ovary color: 143A.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balfaforch', substantially as herein shown and described.

* * * * *